US008552748B2

(12) United States Patent
Simonato et al.

(10) Patent No.: US 8,552,748 B2
(45) Date of Patent: Oct. 8, 2013

(54) ELECTRICAL DETECTION AND/OR QUANTIFICATION OF ORGANOPHOSPHORUS COMPOUNDS

(75) Inventors: Jean-Pierre Simonato, Sassenage (FR); Alexandre Carella, Mazeres Lezons (FR)

(73) Assignee: Commissariat a l'Energie Atomique, Paris (FR)

( * ) Notice: Subject to any disclaimer, the term of this patent is extended or adjusted under 35 U.S.C. 154(b) by 1088 days.

(21) Appl. No.: 12/501,659

(22) Filed: Jul. 13, 2009

(65) Prior Publication Data

US 2010/0033198 A1 Feb. 11, 2010

(30) Foreign Application Priority Data

Jul. 29, 2008 (FR) ..................... 08 04319

(51) Int. Cl.
G01R 27/08 (2006.01)
G01N 27/414 (2006.01)

(52) U.S. Cl.
USPC ............................................ 324/691; 438/49

(58) Field of Classification Search
None
See application file for complete search history.

(56) References Cited

U.S. PATENT DOCUMENTS 5,846,753 A * 12/1998 Akkara et al. ................. 435/18

FOREIGN PATENT DOCUMENTS

| EP | 1 460 130 A1 | 9/2004 |
| WO | WO 02/33732 A3 | 4/2002 |
| WO | WO 2006/099518 A2 | 9/2006 |

OTHER PUBLICATIONS

Trevor J. Dale, et al., "Fluorescent Sensors for Organophosphorus Nerve Agent Mimics", Journal of the American Chemical Society, XP-002518148, vol. 128, No. 14, 2006, pp. 4500-4501.

* cited by examiner

*Primary Examiner* — Jermele M Hollington
*Assistant Examiner* — Trung Nguyen
(74) *Attorney, Agent, or Firm* — Oblon, Spivak, McClelland, Maier & Neustadt, L.L.P.

(57) ABSTRACT

A device for detecting and/or quantifying organophosphorus compounds, including an electrical device including a source electrode and a drain electrode separated by a semiconductive material, characterized in that at least one receptor molecule, including a group R and a primary alcohol in spatial proximity to a tertiary amine, with which the primary alcohol is capable of reacting in the presence of an organophosphorus compound, is grafted, by the group R, onto one of the electrodes or onto the semiconductive material, and a device for detecting the variation in positive charges between the two electrodes.

15 Claims, No Drawings

ELECTRICAL DETECTION AND/OR QUANTIFICATION OF ORGANOPHOSPHORUS COMPOUNDS

The present invention relates to a method and a device for the electrical detection and/or quantification of organophosphorus compounds present in gaseous form or in solution in a solvent.

Organophosphorus compounds are molecules constituted of a phosphate atom to which various chemical groups are bonded, the nature of said groups determining the exact properties of the compound. Organophosphorus compounds, which were the subject of intensive research on combat gases during and after the second world war, which resulted in the development of the gases sarin, soman, tabun, cyclosarin, GV, VX, VE, VG and VM, and of molecules which stimulate the action of neurotoxic organophosphorus compounds, of the type DFP (diisopropylfluorophosphate), DCP (diethylchlorophosphate) and DMMP (dimethylmethylphosphonate), are today mainly used in agriculture as insecticides or herbicides. Among the large variety of organophosphorus compound-based pesticides that exist, mention may in particular be made of parathion, malathion, methyl parathion, chlorpyrifos, diazinon, dichlorvos, phosmet, tetrachlorvinphos and methyl azinphos.

The mode of action of organophosphorus compounds is based on the affinity of the latter for an enzyme involved in nerve impulse transmission: cholinesterase. Organophosphorus compounds in fact have the property of binding particularly strongly and stably to the active site of this enzyme. Once bound, the organophosphorus compound prevents the cholinesterase from degrading acetylcholine, a neurotransmitter released at the level of neuronal synapses during neuronal excitation: through a lack of degradation of acetylcholine to inactive choline and acetyl compounds, the neurones are constantly excited, which may lead to paralysis of the central nervous system and result in death.

Since the mechanism involved in nerve impulse transmission which is blocked by organophosphorus compounds is identical throughout the animal kingdom, the organophosphorus compounds used as insecticides are not only toxic to insects, but also to any animal, including humans. For this reason, despite their relative good biodegradability which has enabled them to replace organochloro compound-based insecticides which have a poor biodegradability, their much greater toxicity requires particular precautions for use. Specifically, organophosphorus compounds can pose very serious problems owing to the accumulation in the environment or all along the food chain in the case of the presence of residues on plants, in water, or in meat from animals having consumed foods containing organophosphorus compounds. Since these insecticides are among those most widely used, not only in agriculture by individuals working in the industry, but also by private individuals, the detection and the quantitative determination of organophosphorus compounds represent a public health interest and would be particularly useful for the agrofoods industry.

In addition, despite being banned in 1997, combat gases are still a threat. On the one hand, the production of combat gases of the sarin, toman or VX type is easy and, on the other hand, since these compounds are odourless and colourless, they can be inhaled without the individual realizing it. The immediate detection of the presence of such gases therefore represents a major issue for protecting soldiers in the combat zone, but also civilian populations in the face of the risk of terrorism. These threats are clearly established, especially since the deadly sarin attack carried out by the terrorist group Aum Shinrikyo in the Tokyo subway in 1995.

Many methods and devices for detecting organophosphorus compounds have been developed.

Thus, chemical sensors sensitive to organophosphorus gases, most of which operate on the "electronic nose" principle, are sold. U.S. Pat. No. 5,571,401, for example, describes a chemical sensor constituted of arrays comprising a resistor composed of nonconductive polymers and of conductive materials: when a chemical molecule comes into contact with the conductive materials, a difference in resistance is then detected. These sensors have the drawback of not being very specific and of being very sensitive to false positives. Sensors based on two-dimensional grids of carbon nanotubes have also been developed (WO 2006/099518), but, although they are very sensitive and detect a large number of molecules, they do not make it possible to obtain a response specific and selective for organophosphorus compounds.

Recently, detection methods selective for organophosphorus compounds in solution, based on measuring fluorescence, have been described. Zhang et al. have shown that, in the presence of a molecule having an amine in spatial proximity to a primary alcohol and a non-planar, flexible and weakly conjugated chromophore, organophosphorus compounds react with the primary alcohol, the phosphate obtained enabling cyclization by intramolecular nucleophilic substitution, stabilizing the chromophore in the plane and resulting in an increase in fluorescence (S.-W. Zhang and T. M. Swager, J. Am. Chem. Soc., 2003, 125, 3420-3421). This cyclization therefore enables detection, by fluorescence, of the organophosphorus agents in solution. The team of J. Rebek, Jr. subsequently showed that some Kemp's acid derivatives comprising a primary alcohol close to a tertiary amine are also good candidates for detecting neurotoxic organophosphorus species (T. J. Dale & J. Rebek, Jr., J. Am. Chem. Soc., 2006, 4500-4501). As S.-W. Zhang et al. had previously shown, when the primary alcohol reacts with an organophosphorus compound, the phosphate obtained enables cyclization by intramolecular nucleophilic substitution and the obtaining of a quaternary ammonium according to the reaction shown in the scheme below:

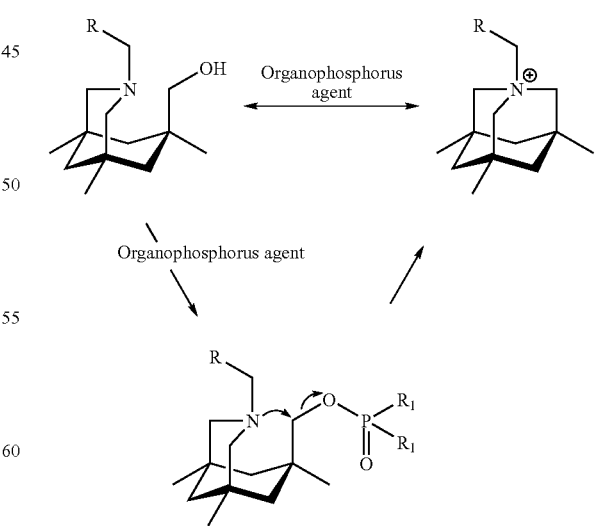

Rebek et al. then developed Kemp's acid derivatives in which R is a fluorophore. In its open form, the fluorescence is prevented by photoinduced electron transfer due to the amine.

The cyclization abolishes this electron transfer and increases the fluorescence of the molecule. A 5-second exposure of a filter comprising Kemp's acid coupled to a fluorophore in an atmosphere comprising 10 ppm of DFP enables the detection of this organophosphorus compound by fluorescence, by reading under a UV lamp. Although this detection is specific, it has various drawbacks. First of all, it must be carried out in a low light-intensity environment. It cannot therefore always be used on premises where the presence of organophosphorus compounds is to be detected and in real time. Furthermore, it requires the use of a UV lamp, which increases the bulk and therefore reduces the portable nature of the device for detecting and/or quantifying the organophosphorus compounds.

Methods based on the use of a biosensor comprising enzymes which have an affinity for organophosphorus compounds, for example cholinesterase, have also been developed. In PCT Application WO 2004/040004, unicellular algae which express acetylcholinesterase at the membrane have been used to test for the presence of organophosphorus compounds in an aqueous medium, the percentage inhibition of acetylcholinesterase being correlated with the concentration of organophosphorus compounds in the control aqueous liquid. This method requires the solubilization of the organophosphorus compounds prior to the detection thereof.

In summary, the methods for detecting organophosphorus compounds that are currently available have the drawback either that they are not selective for organophosphorus compounds, or that they can be used only for testing a sample in solution, or that they require a fluorescence reader and a low light-intensity environment. The development of a rapid, effective and specific method for the selective detection of organophosphorus compounds both in gaseous form and in solution, in any medium, irrespective of the light-intensity thereof, and also the development of a compact and readily portable device for simple, rapid and selective detection therefore still represent major issues in the protection of soldiers in the combat zone and of civilian populations exposed to the risk of terrorism and more broadly for the detection of organophosphorus pesticides.

To this effect, the invention uses the positive charge generated when a "receptor" molecule containing a primary alcohol in spatial proximity to a tertiary amine is placed in the presence of an organophosphorus compound. Exposure of the receptor molecule to an organophosphorus compound leads to the formation of an unstable phosphate ester intermediate by reaction between the primary alcohol and the organophosphorus compound. Intramolecular cyclization through nucleophilic substitution of the phosphate ester intermediate by the tertiary amine, and the formation of a quaternary ammonium, subsequently take place. During the cyclization reaction, a salt is formed, and therefore distinct electric charges (cation and anion) are generated. The generation of a charge through the creation of the ammonium function makes it possible to abruptly modify the electrostatic environment of the molecule.

The team of J. Rebek has shown that this type of receptor molecule reacts with an organophosphorus compound in solution. In particular, in the publication T. J. Dale & J. Rebek, Jr., J. Am. Chem. Soc., 2006, 4500-4501, the cyclization reaction occurs when the organophosphorus compound in gaseous form is brought into contact with a filter paper previously soaked with a solution of Kemp's acid derivative and air-dried.

Unexpectedly, the inventors have noted that the cyclization of a receptor molecule is effective even when said molecule is immobilized on a self-assembled monolayer, or SAM surface. In fact, for such layers, the receptors could have screened one another, which would have to have led to a decrease in reactivity of the receptor.

In the present invention, the presence of organophosphorus compounds is therefore demonstrated by visualizing the modifications of the local electrostatic environment by analysing the variations in resistance, in conductance or in transconductance of an electrical device in which the "receptor" molecule is grafted onto the semiconductive part or one of the electrodes. By virtue of this electrical device, the presence of at least one charge created by the reaction between the organophosphorus compound and the receptor molecule is detected. For the purpose of the present invention, the organophosphorus molecules are organic compounds containing a pentavalent phosphorus atom, and in particular those having the following chemical formula P(=W)XYZ, where W=O or S, and X, Y, Z=any element or group of elements of the Periodic Table.

Thus, a first subject of the invention relates to a device for detecting and/or quantifying organophosphorus compounds, comprising an electrical device comprising:
   a source electrode and a drain electrode separated by a semiconductive material, and at least one receptor molecule comprising a group R and a primary alcohol in spatial proximity to a tertiary amine with which the primary alcohol is capable of reacting in the presence of an organophosphorus compound, the receptor molecule being grafted, by means of the group R, onto one of the electrodes or onto the semiconductive material, and
   a device for detecting the variation in positive charges between the two electrodes.

Advantageously, the receptor molecule is a Kemp's acid derivative and has the following general formula I:

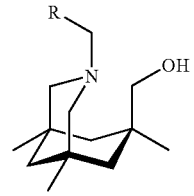

Formula I in which R represents a group comprising a function which makes it possible to graft the receptor molecule onto either of the electrodes or onto the semiconductive material.

The receptor molecule may also be a molecule of general formula II below:

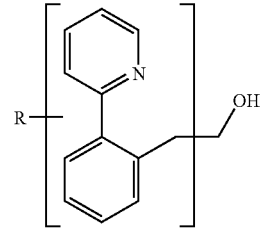

Formula II

The electrical device may be of resistor type, or else of field-effect transistor type.

When the electrical device is of the resistor type, the variation in intensity of the current between the source and drain electrodes, said variation in current intensity being caused by the production of positive charges during the cyclization of the receptor molecule when it comes into contact with the organophosphorus compounds, is, for example, detected and, optionally, measured at a given known voltage applied between the source and drain electrodes. This variation in current intensity gives the variation in conductance.

When the electrical device is of the transistor type, the semiconductive part is composed of a dielectric semiconductive material and also comprises a gate.

Here again, the variation in the intensity of the current is, for example, detected and, optionally, measured at a given known voltage applied between the source and drain electrodes passing through the transistor. Since the intensity of the current is a function of the voltage of the gate, this then gives the transconductance of the transistor.

In the two cases, the variation in conductance or the variation in transconductance reveals the presence of organophosphorus compounds and is proportional to the concentration of organophosphorus compounds.

The receptor molecule is grafted either onto the semiconductive material of the electrical device, or onto the source electrode, or onto the drain electrode. The semiconductive material which plays the role of conduction channel is a semiconductive material, advantageously based on carbon, on silicon, on germanium, on zinc, on gallium, on indium, on cadmium or on an organic semiconductive material.

Preferably, the semiconductive material is constituted of silicon or carbon nanowires and/or nanotubes.

More preferably, the semiconductive material is constituted of silicon nanowire(s) etched onto an SOI (silicon on insulator) surface.

In the case of organic semiconductor materials, the latter may be oligomers, polymers or small molecules. For example, they may be heterocyclic aromatic compounds such as thiophenes and derivatives thereof, preferably P3HT (poly-3-hexylthiophene), or polypyrroles and derivatives thereof, arylamines and derivatives thereof, preferably PTA (polytriarylamine), isochromenones and derivatives thereof, heterocyclic macrocycles such as porphyrins, phthalocyanins and derivatives thereof. The organic semiconductive materials may also be aromatic polycyclic acenes and derivatives thereof, preferably anthracene or pentacene, arylenes and derivatives thereof, for example perylene, poly(para-phenylene), poly(para-phenylene vinylene) or polyfluorene, polysilanes and derivatives thereof.

The electrodes may be metal electrodes, for example made of gold, silver, palladium, platinum, titanium, doped silicon, copper or nickel.

The group R comprises a function for grafting the receptor molecule onto the semiconductive material or the electrodes.

The function for the grafting is in particular selected from: saturated or unsaturated, monocyclic or polycyclic, aromatic hydrocarbon; alkene (of vinyl type, for example); alkyne (of acetylene type, for example); trihalosilane or trialkoxysilane compound; diazo compound, diazonium salts and derivatives; azides; free-radical precursor; isocyanates and derivatives, organometallic compounds and derivatives (for example of lithium compound, organomagnesium compound or zinc compound type); sulphur-containing derivatives such as thiols and mercaptans; carboxylic and/or sulphonic and/or phosphoric acids and ester derivatives thereof; alcohols, phenols; amines, amides; halides. Thus, the group R is, for example, an ethynylphenyl, a vinylphenyl, a diazophenyl or else a pyrene.

The part dedicated to the grafting of the group R is suitable for the material chosen.

For example, for silicon, the part dedicated to the grafting may be an alkyne, an alkene, a diazonium salt, a triazene or a free-radical precursor. The silicon may be coated with a fine layer of oxide, such as native oxide, for example. In this case, the part dedicated to the grafting may be a silane compound (for example, a trialkoxysilane or a trihalosilane) or any other species which binds to the surface of the oxide.

In all cases, the grafting of the receptor part may be carried out in one or more steps. It is, for example, possible to react the surface of the semiconductor with a first molecule, and to subsequently react a function of this grafted molecule with a second organic molecule comprising the organophosphorus-compound receptor part. For example, steps for protection/deprotection of the alcohol function may be envisaged. It is also possible to graft the organophosphorus-compound-sensitive molecule onto a prefunctionalized substrate comprising reactive functions, for example of hydride or hydroxyl type, or else one of the functions specified above.

For example, the silicon, or the native oxide thereof, may be functionalized with a first series of organic molecules comprising end functions onto which the receptor molecule will be grafted in a second step by means of conventional organic, organometallic or inorganic synthesis techniques.

Assemblies by covalent bonding or by means of stabilizing weak interactions are possible. For example, assembly by pi-pi bonding (stabilizing orbital overlap) can be envisaged, preferably in the case of carbon nanotubes.

When one or more carbon nanotubes is (are) used as semiconductive material, the part dedicated to the grafting may be:
- a diazonium salt, a triazene, any free-radical precursor, or any molecule capable of forming covalent bonds with carbon atoms of the carbon nanotubes;
- an aromatic group (for example pyrene, anthracene, porphyrin, etc.) or a derivative of the amine family which enables noncovalent (supramolecular) functionalization of the nanotubes;
- an amine or an alcohol for a reaction with the carboxylic acids present at the surface of the carbon nanotubes, optionally after chemical activation (for example, with a coupling agent) for the formation of esters or of amides.

In the case of a germanium-based semiconductive material, the part dedicated to the grafting may, for example, be an alkyne or an alkene.

When the semiconductive material is an indium gallium arsenide (InGaAs), the grafting function may be a sulphur-containing compound, for example a thiol.

In the case of a semiconductive material based on cadmium selenide (CdSe) or on cadmium sulphide (CdS), the grafting function may be an amine or a sulphur-containing compound, for example a thiol.

If the semiconductive material is a zinc oxide, the grafting function may be a carboxylic or phosphoric acid.

If the semiconductive material is a zinc sulphide (ZnS), the grafting function is a sulphur-containing compound, for example a thiol.

In the case of organic semiconductors, the receptor will be integrated during the synthesis of the organic material.

When one of the electrodes is functionalized and when said electrode is made of gold, sulphur-containing organic derivatives such as, for example, a thiol, a protected thiol (thioacetate, for example), a disulphide, or the like, may be used.

Advantageously, the group R of the "receptor" molecule comprises, in addition to a function dedicated to the grafting onto the semiconductive material or onto the electrodes, a "spacer" part which makes it possible to modulate the distance between the receptor molecule and the semiconductive material or the electrodes.

The "spacer" part of the group R may be a $C_1$ to $C_{20}$ alkyl group that may contain one or more heteroatoms, and/or an aromatic radical, and/or a heteroaromatic radical.

The simple structure of the device enables a low-cost, large-scale production. In addition, owing to this simple structure, the device may be very small in size, requiring little energy in order to operate, promoting its portable nature.

Another subject of the present invention relates to a method for detecting and/or quantifying organophosphorus compounds, comprising the following steps:

a) placing the test sample in liquid form or in gaseous form in the presence of a detecting device according to the invention as defined above;

b) evidencing the positive charges generated by the reaction for intramolecular cyclization of the receptor molecule induced by the organophosphorus compound by detecting and/or measuring the difference in resistance, in conductance or in transconductance of said device.

The present invention will be understood more clearly from the further description which follows, which refers to an example given by way of nonlimiting illustration of preparation of the detecting device in accordance with the invention and to the use thereof in a method for detecting an organophosphorus compound.

EXAMPLE 1

Fabrication of a Sensor of the Pseudo-MOS Transistor Type 1.1. Production of the Test Device Electrical devices were fabricated on SOI where the semiconductive material is an etched silicon nanowire 280 nm wide, 4 μm long and 16 nm thick, etched onto a layer of silicon oxide 77 nm thick.

1.2. Synthesis of the Receptor

A receptor in which the function R is 4-ethynylbenzyl was synthesized using Kemp's triacid. In a first step, the Kemp's triacid is converted to anhydride (product 1) by reflux in thionyl chloride. After evaporation of the residual thionyl chloride, the product 1 is reacted with 4-iodobenzylamine in pyridine at reflux, and then treated with trimethylsilyldiazomethane. A Sonogashira reaction makes it possible to introduce an alkyne protected with a trimethylsilyl group. Treatment of the molecule 3 with $LiAlH_4$ makes it possible to reduce the imide and ester groups so as to give, respectively, amine and alcohol groups. Unexpectedly, deprotection of the silylated group is observed. Cyclization of the Kemp's derivative 4 obtained by treatment with DFP was carried out in an NMR tube. The cyclization is complete.

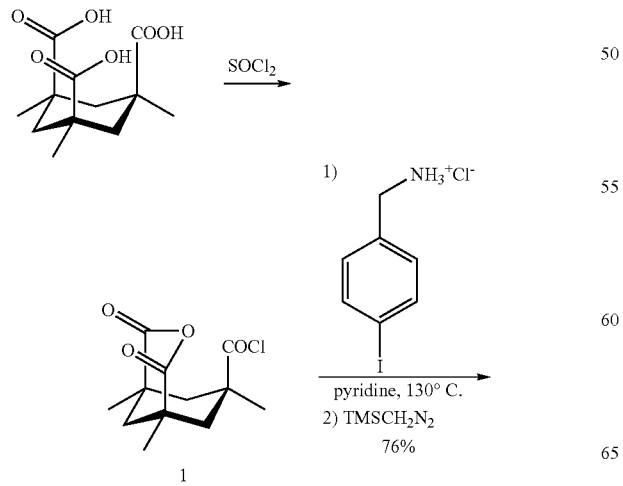

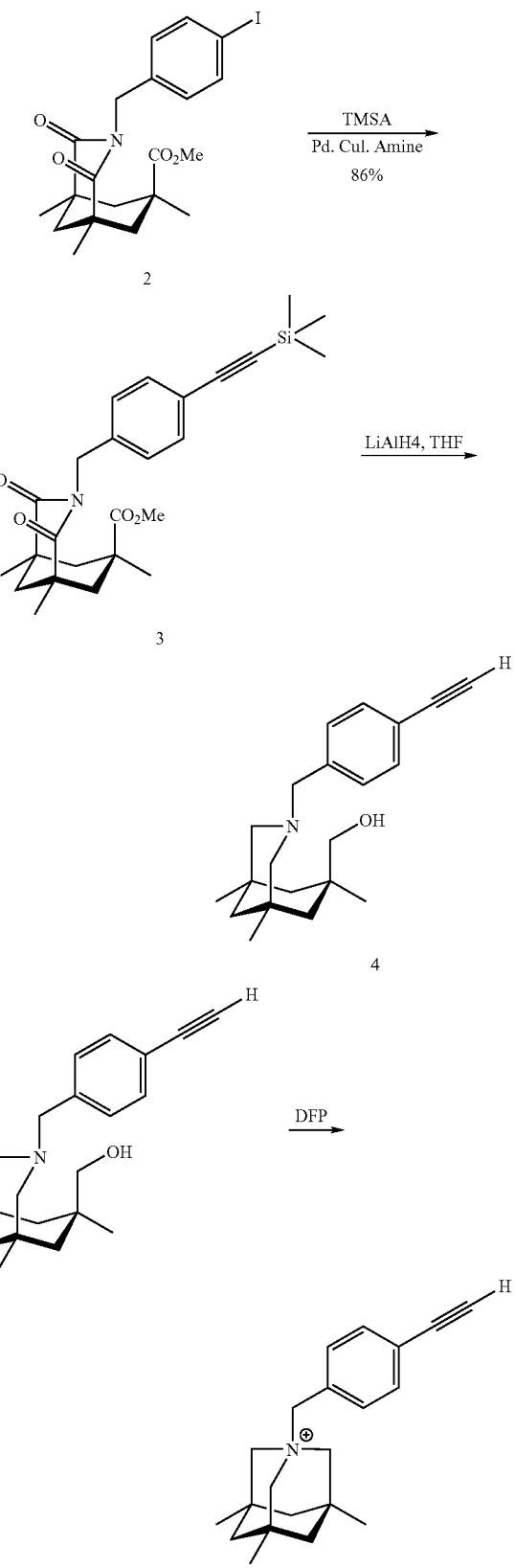

1.3. Grafting of the Receptor onto the Test Device

The receptor is grafted onto the test device by thermal hydrosilylation. The device is cleaned with a piranha solution, constituted of a 3-to-1 mixture of concentrated sulphuric acid and of aqueous hydrogen peroxide at 30%, and then treated with a solution of HF at 1% by weight. The activated device is refluxed in a 0.5 mM solution of the receptor 4 in mesitylene.

EXAMPLE 2

Detection of Organophosphorus Compounds by the Sensor

The device obtained in Example 1 was used to detect the presence of organophosphorus compounds. For this, the device according to the invention was placed in a chamber containing diisopropylfluorophosphate vapours (10 ppm) for one minute.

In its open form (prior to reaction with an organophosphorus molecule), the receptor is a neutral molecule (no electrostatic charge). The reaction with an organophosphorus molecule, in this example diisopropylfluorophosphate, results in cyclization and the production of a charge in the form of an ammonium. The generation of this charge is detected electrically by modification of the conductance of the device. Under the conditions indicated above, a relative variation in conductance ($\Delta g/g$) of greater than 5% was measured.

The invention claimed is:

1. An apparatus for detecting and/or quantifying organophosphorus compounds, comprising:
    an electrical device comprising a source electrode and a drain electrode separated by a semiconductive material, wherein at least one receptor molecule, comprising a group R and a primary alcohol in spatial proximity to a tertiary amine, with which the primary alcohol is capable of reacting in the presence of an organophosphorus compound, is grafted, by means of the group R, onto one of the source or drain electrodes or onto the semiconductive material, and
    a device for detecting the variation in positive charges between the two electrodes, wherein
    the at least one receptor molecule has the general formula:

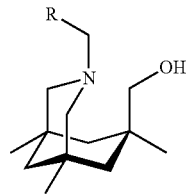

in which R is a group comprising a function that enables the at least one receptor molecule to be grafted onto at least one of the source electrode, the drain electrode and the semiconductive material.

2. The apparatus according to claim 1, wherein the semiconductive material is chosen from materials based on carbon, silicon, germanium, zinc, gallium, indium, cadmium or an organic semiconductive material.

3. The apparatus according to claim 1 or 2, wherein the semiconductive material is constituted of silicon nanowire(s) and/or carbon nanotube(s).

4. The apparatus according to claim 1, wherein the semiconductive material is a silicon nanowire.

5. The apparatus according to claim 1, wherein a material of the source and drain electrodes is gold, silver, palladium, platinum, titanium, doped silicon, copper or nickel.

6. The apparatus according to claim 1, wherein said electrical device is of resistor type.

7. The apparatus according to claim 1, wherein said electrical device is of field-effect transistor type.

8. The apparatus according to claim 1, wherein the semiconductive material is silicon, the at least one receptor molecule is grafted onto said semiconductive material, and a grafting function of the group R of the at least one receptor molecule, dedicated to the grafting, is an alkyne, an alkene, a diazonium salt, a triazene or a free-radical precursor.

9. The apparatus according to claim 1, wherein the semiconductive material is constituted of carbon nanotubes, the at least one receptor molecule is grafted onto said semiconductive material, and a grafting function of the group R of the at least one receptor molecule, dedicated to the grafting, is a diazonium salt, a triazene, a free-radical precursor, an aromatic group, a derivative of the amine family which enables noncovalent functionalization of the nanotubes, an amine or an alcohol.

10. The apparatus according to claim 1, wherein the semiconductive material is germanium-based, the at least one receptor molecule is grafted onto said semiconductive material, and a grafting function of the group R of the at least one receptor molecule, dedicated to the grafting, is an alkyne or an alkene.

11. The apparatus according to claim 1, wherein the semiconductive material is constituted of indium gallium arsenide (InGaAs), the at least one receptor molecule is grafted onto said semiconductive material, and a grafting function of the group R of the at least one receptor molecule, dedicated to the grafting, is a sulphur-containing compound.

12. The apparatus according to claim 1, wherein the semiconductive material is based on cadmium selenide (CdSe) or on cadmium sulphide (CdS), the at least one receptor molecule is grafted onto said semiconductive material, and a grafting function of the group R of the at least one receptor molecule, dedicated to the grafting, is an amine or a sulphur-containing compound.

13. The apparatus according to claim 1, wherein the semiconductive material is zinc oxide-based, the at least one receptor molecule is grafted onto said semiconductive material, and a grafting function of the group R of the at least one receptor molecule, dedicated to the grafting, is a carboxylic acid or a phosphoric acid.

14. The apparatus according to claim 1, wherein the semiconductive material is zinc sulphide-based, the at least one receptor molecule is grafted onto said semiconductive material, and a grafting function of the group R of the at least one receptor molecule, dedicated to the grafting, is a sulphur-containing compound.

15. The apparatus according to claim 1, wherein the source and drain electrodes are made of gold, the at least one receptor molecule is grafted onto one of the source or drain electrodes, and a grafting function of the group R of the at least one receptor molecule, dedicated to the grafting, is a sulphur-containing organic derivative.

* * * * *